US005795780A

United States Patent [19]
Cederholm-Williams et al.

[11] Patent Number: 5,795,780
[45] Date of Patent: Aug. 18, 1998

[54] METHOD OF USE OF AUTOLOGOUS THROMBIN BLOOD FRACTION IN A CELL CULTURE WITH KERATINOCYTES

[75] Inventors: Stewart A. Cederholm-Williams, Oxford, United Kingdom; Ulla Weis-Fogh, Hoersholm, Denmark

[73] Assignee: Bristol-Myers Squibb Company, Skillman, N.J.

[21] Appl. No.: 752,459

[22] Filed: Nov. 15, 1996

Related U.S. Application Data

[62] Division of Ser. No. 465,154, Jun. 5, 1995, which is a continuation of Ser. No. 81,532, Jun. 23, 1993, abandoned.

[51] Int. Cl.$^6$ .................. C12N 5/06; C12N 5/22
[52] U.S. Cl. ............... 435/371; 435/214; 424/94.64
[58] Field of Search ............ 424/94, 64; 435/214, 435/371

[56] References Cited

U.S. PATENT DOCUMENTS

| | | | |
|---|---|---|---|
| 4,265,233 | 5/1981 | Sugitachi et al. | 128/156 |
| 4,363,319 | 12/1982 | Altshuler | 128/156 |
| 4,374,830 | 2/1983 | Schneider | 424/177 |
| 4,377,572 | 3/1983 | Schwarz et al. | |
| 4,627,879 | 12/1986 | Rose et al. | 106/124 |
| 4,696,812 | 9/1987 | Silbering et al. | 424/94.64 |
| 4,714,457 | 12/1987 | Alterbaum | |
| 4,752,466 | 6/1988 | Saferstein et al. | 424/46 |
| 4,923,815 | 5/1990 | Tanaka et al. | 435/183 |
| 4,965,203 | 10/1990 | Silbering et al. | 435/188 |
| 5,089,415 | 2/1992 | La Duca | |
| 5,099,003 | 3/1992 | Kotitschke et al. | |
| 5,130,244 | 7/1992 | Nishimaki et al. | 435/188 |
| 5,143,838 | 9/1992 | Kraus et al. | 435/214 |
| 5,151,355 | 9/1992 | Crowley et al. | |
| 5,165,938 | 11/1992 | Knighton | 424/532 |
| 5,185,001 | 2/1993 | Galanakis | |
| 5,219,328 | 6/1993 | Morse et al. | 604/49 |
| 5,290,552 | 3/1994 | Sierra et al. | 424/94.64 |
| 5,304,372 | 4/1994 | Michalski et al. | 424/94.64 |
| 5,393,666 | 2/1995 | Linnau | 435/183 |
| 5,443,959 | 8/1995 | Kikuchi et al. | 435/13 |
| 5,474,770 | 12/1995 | Broly et al. | 424/94.64 |
| 5,506,127 | 4/1996 | Proba et al. | 435/214 |
| 5,510,102 | 4/1996 | Cochrum | 424/78.08 |

FOREIGN PATENT DOCUMENTS

| | | |
|---|---|---|
| 0 443 724 A1 | 8/1991 | European Pat. Off. |
| 0 505 604 A1 | 9/1992 | European Pat. Off. |
| 0505604 | 9/1992 | European Pat. Off. |
| 0 534 178 A2 | 3/1993 | European Pat. Off. |
| 1527261 A1 | 12/1989 | U.S.S.R. |
| WO86/01814 | 3/1986 | WIPO |
| WO88/02259 | 4/1988 | WIPO |
| WO88/03151 | 5/1988 | WIPO |
| WO91/09641 | 7/1991 | WIPO |
| WO93/19805 | 10/1993 | WIPO |

OTHER PUBLICATIONS

Brennan, Blood Reviews, vol. 5(4), pp. 240–244, 1991.
Thompson et al., Drug Intell. Clin. Pharm., vol. 22(12), pp. 946–952, 1988.
Ronfard, V. et al., Burns, vol. 17(3), pp. 181–184, 1991.
Sakuragawa, N. et al., Acta Medica et Biologica, vol. 23(1), pp. 65–73, 1975.
Awano, K. et al., Journal of Cardiovascular Pharmacology, vol. 13(5), pp. 781–792, 1989.
Kotelba–Witkowski, B. et al., Transfusion, vol. 22(2), pp. 121–124, Mar./Apr.,1982.
Martin, M. et al., Thrombolytic Therapy, vol. 47, pp. 235–241, 1971.
Tsvetkov, TS. et al., Cryobiology, vol. 21(6), pp. 661–663, 1984.
Georgi, M. et al., Dtsh. med. Wschr., vol. 100(47), pp. 2428–2429 plus English translation, Nov. 1975.
Suzuki, S. et al., Thrombosis Research, vol. 53(3), pp. 271–277, 1989.
Mann, K.G. et al., Thrombin Peptides, vol. 244(43), pp. 6555–6557, Dec. 1969.
Fischer, A.M. et al., Journal of Chromatography, vol. 363(1), pp. 95–100, 1986.
Mann, K.G. et al., J. Biol. Chem., vol. 246(19), pp. 5994–6001, 1971.
Yu, X.J. et al., Journal of Chromatrography, vol. 376, pp. 429–435, 1986.
Rosenberg, R.D. et al., Fed. Proc., vol. 28(2), p. 321, abstract #361, 1969.
Redl, H. et al., Biomaterials, vol. 4(1), pp. 29–32, Jan. 1983.
Nowotny, R. et al., Biomaterials 1980, vol. 3, pp. 677–682, ed. G.D. Winter et al, 1982.
Lundblad, R.L. et al., Biochemical and Biophysical Research Communications, vol. 66(2), pp. 482–489, 1975.
Redl, H. et al., Fibrinkleber Orthop. Traumatol. Orthop., vol. 4, pp. 178–181 plus English translation, 1982.
Adams D.H., "Bovine spongiform encephalopathy–a new disease transmissable to humans?" Medical Hypothesis 32:313–317 (1990).
Allary et al., "Isolation of the human thrombin by affinity chromatography for an utilisation in the preparations of fibrin glue" Ann. Pharmaceutiques Francaises 48(3):129–135 (1990). (With English Translation of Entire Article).
Alterbaum et al., "Autologous fibrin glue (a new method of preparation)" Surgical Forum (41st Annual Forum on Fundamental Surgical Problems Held at the 71st Annual Clinical Congress of the American College of Surgeons, Chicago) 36:544–547 (1985).
Andrianova et al., "An accessible method of simultaneous preparation of pure fibrinogen and thrombin from blood plasma" Lab Delo (USSR) 11:648–650 (1975). (With English Translation of Entire Article).

(List continued on next page.)

Primary Examiner—Chhaya D. Sayala
Attorney, Agent, or Firm—Theodore R. Furman, Jr.; John M. Kilcoyne

[57] ABSTRACT

The subject invention relates to the use of thrombin in a medical procedure in an animal. More specifically, the subject invention relates to such use of thrombin wherein the thrombin is a thrombin blood fraction, is autologous to that animal.

2 Claims, No Drawings

OTHER PUBLICATIONS

Blomback et al., "Purification of human and bovine fibrinogen" Arkif For Kemi 10(29):415–443 (1956).

Burnouf–Radosevich et al., "Properties of a solvent–detergent treated fibrin glue" Colloque Inserm 175:89–100 (1989).

Clark et al., "Strategy for purification of coagulation factor concentrates" Annals of Clinical and Laboratory Science 19(3):196–207 (1989).

Cohn et al., "Preparation and properties of serum and plasma proteins" 68:459–475 (1946).

Committee for Proprietary Medicinal Products, "EEC Regulatory Document Note for Guidance—Validation of virus removal and inactivation procedures" Biologicals 19:247–251 (1991).

Dresdale et al., "Hemostatic effectiveness of fibrin glue derived from single–donor fresh frozen plasma" Annals of Thoracic Surgery 40(4):385–387 (1985).

Dulchavsky et al., "Autologous fibrin gel: bactericidal properties in contaminated hepatic injury" Journal of Trauma 31(7):991–995 (1991).

Durham et al., "A method for preparation of fibrin glue" Journal of Laryngology and Otology 101:1182–1186 (1987).

Ederle et al., "Does the combination of a human fibrin sealant with ranitidine accelerate the healing of duodenal ulcer?" Ital. J. Gastroenterol. 23:354–356 (1991).

Epstein et al., "A new autologous fibrinogen–based adhesive for otologic surgery" Ann. Otol. Rhinol. Laryngol. 95:40–45 (1986).

Everberg et al., "'How I do It'–Otology and neurotology–Autologous tissue seal in myringoplasty" Laryngoscope 97:370–371 (1987).

Feldman et al., "Compatibility of autologous fibrin adhesive with implant materials" Arch. Otolaryngol. Head Neck Surg. 114:182–185 (1988).

Furlan M., "Purification of fibrinogen" Curr. Probl. Clin. Biochem 14:133–145 (1984).

Furtado et al., "Comparative study of nine Bothrops snake venoms from adult female snakes and their offspring" Toxicon. 29(2):219–226 (1991).

Gibble et al., "Fibrin glue: the perfect operative sealant?" Transfusion 30(8):741–747 (1990).

Gestring et al., "Autologous fibrinogen for tissue–adhesion, hemostasis and embolization" Vascular Surgery Sep./Oct.: 294–304 (1983).

Gestring et al., "Hemostasis with autologous fibrinogen" Acta. Chir. Austriaca 2:46–48 (1981).

Harris et al., "Autologous fibrin tissue adhesive" Laryngoscope 95:1074–1076 (1985).

Harris et al., "Extended experimental and preliminary surgical findings with autologous fibrin tissue adhesive made from patient's own blood" Laryngoscope 96:1062–1064 (1986).

Harris et al., "Autologous fibrin tissue adhesive: factors influencing bonding power" laryngoscope 98:731–733 (1988).

Hartman et al., "Autologous whole plasma fibrin gel" Arch. Surg. 127:357–359 (1992).

Hilfenhaus et al., "Fibrin glue safety: inactivation of potential viral contaminants by pasteurization of the human plasma components" Drug Res. 35(2):1617–1619 (1985).

Jabs et al., "The effect of fibrin glue on skin grafts in infected sites" Plastic and Reconstructive Surgery 89(2):268–271 (1992).

Kazal et al., "The preparation and some properties of fibrinogen precipitated from human plasma by glycine" P.S.E.B.M. 113:989–994 (1963).

Kekwick et al., "The purification of human fibrinogen" Bioch. 60:671–683 (1955).

Laitakari et al., "Autologous and homologous fibrinogen sealants: adhesive strength" Laryngoscope 99:974–976 (1989).

Latallo Z.S., "Report of the task force on clinical use of snake venom enzymes" Thrombosis and Haemostasis 39(3):768–774 (1978).

Marshall S., "Commercial fibrinogen, autogenous plasma, whole blood and cryoprecipitate for coagulum pyelolithotomy: a comparative study" Journal of Urology 119:310–311 (1978).

Masri et al., "Isolation of human fibrinogen of high purity and in high yield using polyethylene glycol 1000" Thrombosis and Haemostatsis 49(2):116–119 (1983).

Mattock et al., "Differences in the subunit structure of human fibrin formed by the action of arvin, reptilase and thrombin" Nature New Biology 233:277–279 (1971).

Moretz Jr. et al, "A simple autologous fibrinogen glue for otologic surgery" Otolaryngology–Head and Neck Surgery 95(1):122–124 (1986).

Mosesson et al., "The preparation and properties of human fibrinogen of relatively high solubility" Biochemistry 5(9):2829–2835 (1966).

Ness et al., "Cryoprecipitate as a reliable source of fibrinogen replacement" JAMA 241(16):1690–1691 (1979).

Ney et al., "Fibrin glue–antibiotic suspension in the preservation of prosthetic graft infection" Journal of Trauma 30(8):1000–1006 (1990).

Pfluger et al., "Partial rat kidney resection using autologous fibrinogen thrombin adhesive system" Urol. Res. 9:105–110 (1981).

Polson et al., "The fractionation of protein mixtures by linear polymers of high molecular weight" Biochimica Et Biophysica Acta 82:463–475 (1964).

Quick et al., "Production of thrombin from precipitate obtained by acidification of diluted plasma" Am. J. Physiol. 183:114–118 (1955).

Seelich T., "Tissucol® (Immuno, Vienna): Biochemistry and methods of application" J. Head and Neck Pathol. 3:65–69 (1982).

Siedentop et al., "Autologous fibrin tissue adhesive biodegration and systemic effects" Laryngoscope 97:1141–1144 (1987).

Sierra D.H., "Fibrin sealant adhesive systems: a review of their chemistry, material properties and clinical applications" J. Biomaterials Applications 7:309–352 (1993).

Silberstein et al., "An autologous fibrinogen–based adhesive for use in otologic surgery" Transfusion 28(4):319–321 (1988).

Spotnitz et al., "Fibrin glue from stored human plasma" The American Surgeon 53(8):460–462 (1987).

Stammberger H., "Re: The concentrated autologous tissue glue (CATG)" Am. J. Otology 5(5):424–425 (1984).

Torsiglieri et al., "Biochemical characterization of autologous fibrinogen adhesive" Laryngoscope 97:1186–1190 (1987).

Vila et al., "A rapid method for isolation of fibrinogen from human plasma by precipitation with polyethylene glycol 6,000" Thrombosis Research 39:651–656 (1985).

Weis–Fogh U.S., "Fibrinogen prepared from small blood samples for autologous use in a tissue adhesive system" Eur. Surg. Res. 20:381–389 (1988).

Wolf G., "The concentrated autologous tissue glue" Arch Otolaryngol. 237:279–283 (1983). (With English Translation of Entire Article).

METHOD OF USE OF AUTOLOGOUS THROMBIN BLOOD FRACTION IN A CELL CULTURE WITH KERATINOCYTES

This is a divisional of application Ser. No. 08/465,154 filed Jun. 5, 1995, which is a continuation of application Ser. No. 08/081,532 filed Jun. 23, 1993, now abandoned.

FIELD OF THE INVENTION

The subject invention relates to the use of thrombin in a medical procedure in an animal. More specifically, the subject invention relates to such use of thrombin wherein the thrombin is a thrombin blood fraction, as defined hereinbelow.

BACKGROUND OF THE INVENTION

One mechanism for hemostasis, i.e., prevention of blood loss, of an animal is the formation of a blood clot. Clot formation, i.e., blood coagulation, occurs by means of a complex cascade of reactions with the final steps being the conversion of fibrinogen by thrombin, calcium ions and activated factor XIII to form the fibrin clot. For a review of the mechanisms of blood coagulation and the structure of fibrinogen, see C. M. Jackson, Ann. Rev. Biochem., 49:765–811 (1980) and B. Furie and B. C. Furie, Cell, 53:505–518 (1988).

Thrombin, which is a proteolytic enzyme, is derived from prothrombin. Prothrombin is converted to thrombin by calcium and prothrombinase. Prothrombinase is formed through a cascade of reactions that begins with the proteins factor XI and factor XII.

A fibrin sealant is a biological adhesive whose effect imitates the final stages of coagulation, thereby resulting in a fibrin clot. Conventional fibrin sealants generally consist of concentrated human fibrinogen, bovine aprotinin and factor XIII, as the first component and bovine thrombin and calcium chloride as the second component. Application is generally carried out with a double-barrelled syringe, which permits simultaneous application of both components to the site where one wants to form the fibrin clot. Aprotinin is a fibrinolytic inhibitor added to promote stability of fibrin sealants.

The fibrinogen component of the fibrin sealant is prepared from pooled human plasma. The fibrinogen can be concentrated from the human plasma by cryoprecipitation and precipitation using various reagents, e.g., polyethylene glycol, ether, ethanol, ammonium sulfate or glycine. For an excellent review of fibrin sealants, see M. Brennan, Blood Reviews, 5:240–244 (1991); J. W. Gibble and P. N. Ness, Transfusion, 30:741–747 (1990); H. Matras, J. Oral Maxillofac Surg., 43:605–611 (1985) and R. Lerner and N. Binur, J. of Surgical Research, 48:165–181 (1990).

Recently, there has also been an interest in the preparation of fibrin sealants that utilize autologous fibrin. An autologous fibrin sealant is a fibrin sealant wherein the fibrinogen component of the fibrin sealant is extracted from the patients own blood. The use of an autologous fibrin sealant is preferred because it eliminates the risk of transmission of blood-transmitted infections, e.g., hepatitis B, non A, non B hepatitis and acquired immune deficiency syndrome (AIDS), that could otherwise be present in the fibrinogen component extracted from pooled human plasma. See L. E. Silberstein et al., Transfusion, 28:319–321 (1988); K. Laitakari and J. Luotonen, Laryngoscope, 99:974–976 (1989) and A. Dresdale et al., The Annals of Thoracic Surgery, 40:385–387 (1985).

An infection can be transmitted by a fibrin sealant not only by means of the fibrinogen but also by means of the bovine aprotinin and the bovine thrombin component. Bovine thrombin has been known to carry the infectious agent bovine spongiform encephalitis (BSE) and other viruses pathogenic to mammals. Furthermore, bovine thrombin is a potential antigen, which can cause immunological reactions in humans. Thus, the use of bovine thrombin could result in the recipient of the bovine thrombin being adversely affected. See D. M. Taylor, J. of Hospital Infection, 18(Supplement A):141–146 (1991), S. B. Prusiner et al., Cornell Vet, 81 No. 2: 85–96 (1991) and D. Matthews, J. Roy. Soc. Health, 3–5 (February 1991).

Accordingly, there is the need for a sealant that utilizes thrombin that can be delivered to a patient without the risk of viral contamination or other adverse affects.

SUMMARY OF THE INVENTION

The subject invention relates to a method for utilizing thrombin in a medical procedure in an animal, the improvement comprising thrombin that is a thrombin blood fraction in which said thrombin blood fraction comprises:

(a) a thrombin concentration of from about 1 NIH unit/ml to about 2,000 NIH units/ml, and (b) a specific activity of thrombin of from about 1 NIH unit/mg of blood protein to about 200 NIH units/mg of blood protein, wherein said thrombin blood fraction is substantially free of active antithrombin III.

The subject invention also relates to a method for preparing a prothrombin blood fraction from whole blood comprising:

(a) diluting whole blood to an ionic strength of less than about 100 millimolar;

(b) separating plasma from said whole blood;

(c) lowering the pH of said plasma to precipitate a prothrombin blood fraction; and (d) separating said prothrombin blood fraction from said plasma.

The prothrombin blood fraction is then redissolved and converted to thrombin, i.e., the thrombin blood fraction is formed, which can then be utilized in a medical procedure in an animal, e.g., as a component of a fibrin sealant.

DETAILED DESCRIPTION OF THE INVENTION

The subject invention relates to the use of a thrombin blood fraction, as defined hereinbelow, in a medical procedure, e.g., as a component of a fibrin sealant, in an animal, preferably a mammal. Suitable mammals include a human, a cow, a pig, a dog and a rabbit, or other mammals that have an adequate blood volume to prepare the thrombin blood fraction. The thrombin blood fraction can be prepared from whole blood and is impure in that it contains blood proteins other than thrombin. However, the thrombin blood fraction can be prepared very simply and rapidly, e.g., in less than about one or two hours, and is believed to be as efficacious as a highly pure thrombin preparation.

The thrombin blood fraction can be prepared from whole blood. It is preferred that the whole blood be obtained from a single individual animal. Also, it is preferred that the thrombin blood fraction be administered to the same individual animal from which the whole blood was taken. Thus, one aspect of the invention is the use of an autologous thrombin blood fraction in a medical procedure. In this embodiment, there is also no risk of transmission of blood-transmitted infections because the thrombin blood fraction is to be administered to the same individual animal that donated the whole blood. Also, for the same reason, the blood proteins other than thrombin that are present in the thrombin blood fraction would not be antigenic.

Furthermore, since the thrombin blood fraction is preferred to be prepared from a single individual animal and used in the same, generally small volumes of whole blood are required, especially since it is also preferred to prepare a thrombin blood fraction for a single use. Also, it is preferred to prepare the fraction within several hours of the time of use. It is preferred that from about 10 ml to about 50 ml, more preferably from about 10 ml to about 30 ml and most preferably from about 10 ml to about 20 ml of whole blood be utilized to prepare the thrombin blood fraction of the subject invention.

The thrombin blood fraction of the subject invention has a thrombin concentration of from about 1 NIH unit to about 2,000 NIH units, preferably from about 100 NIH units to about 800 NIH units and most preferably from about 100 NIH units to about 500 NIH units per ml of the thrombin blood fraction.

It is believed that at such concentrations the thrombin blood fraction possesses a sufficient thrombin concentration for the desired medical use. Of course, the preferred thrombin concentration depends on the medical use of the thrombin blood fraction.

The thrombin concentration of the thrombin blood fraction can be determined by measuring the coagulation time of a standard fibrinogen solution after addition of the thrombin blood fraction in a suitable diluted form. As a reference, standard thrombin solutions, containing from 2 to 15 NIH units/ml, can be utilized.

The thrombin blood fraction of the subject invention has a specific activity of thrombin of from about 1 NIH unit to about 200 NIH units, preferably from about 5 NIH units to about 100 NIH units and most preferably from about 5 NIH units to about 50 NIH units per mg. of total blood protein. Such lower specific activities of the thrombin blood fraction are believed to be as effective in a medical procedure as the more pure thrombin blood fractions. However, such lower specific activity of the thrombin blood fractions can be prepared more readily.

The specific activity of the thrombin blood fraction is, in essence, a measurement of the amount of thrombin per amount of blood protein in the thrombin blood fraction. Thus, the specific activity of the thrombin blood fraction of the subject invention is quite low relative to thrombin preparations that have been prepared heretofore. For example, U.S. Pat. No. 5,143,838 discloses a thrombin preparation with a specific activity of at least 800 NIH units per mg. of total protein. Also, U.S. Pat. No. 5,151,355 discloses a thrombin preparation with a specific activity of greater than 1,000 NIH units/mg. of total protein. Although the specific activity of the thrombin blood fraction of the subject is low, never the less it is believed that the blood fraction is efficacious for use in medical procedures.

The specific activity of the thrombin blood fraction of the subject invention can be calculated by measuring the thrombin concentration (NIH units/ml) and by dividing that number by the protein concentration (mg/ml) measured by any standard protein assay, e.g., UV absorbance.

The thrombin blood fraction is also substantially free of active antithrombin III. For the purpose of the subject invention, "substantially free of active antithrombin III" means that the thrombin blood fraction per unit volume contains an amount of active antithrombin III that is less than about 50% by activity of antithrombin III in normal plasma per unit volume. It is preferred that such percentage be less than about 30%, more preferably less than about 10% and most preferably less than about 5%. It is essential that the antithrombin III either be removed from or inactivated in the thrombin blood fraction. Otherwise, antithrombin III will prevent the conversion of the prothrombin in the blood fraction to thrombin and/or inactivate the thrombin that is formed.

It is preferred that the thrombin blood fraction also be substantially free of fibrinogen and fibrin. For the purpose of the subject invention, substantially free of fibrinogen and fibrin means that the thrombin blood fraction per unit volume contains an amount of fibrinogen plus fibrin that is less than about 1% by weight of fibrinogen in normal plasma per unit volume. It is preferred that fibrinogen not be present in the thrombin blood fraction because the thrombin will convert the fibrinogen to fibrin, which will polymerize to form a clot, thereby rendering the thrombin blood fraction impracticable. The fibrinogen itself can be removed from the thrombin blood fraction or the fibrinogen can be removed as the fibrin clot, thereby, of course, also removing the fibrin. However, the fibrinogen need not be removed if, for example, the thrombin is inactivated as described in patent publication PCT/US91/00003.

The thrombin blood fraction can be utilized immediately after it is prepared. If the fraction is not utilized immediately after its preparation, the fraction can be stored. Storage of the fraction requires that the fraction be preserved by, for example, freezing or lyophilizing the fraction or holding the composition at 4° C. The fraction in frozen or lyophilized form will be stable for a period of months. When the fraction is held at 4° C., it is stable for at least a period of days.

If the fraction is frozen, the fraction must be thawed at the time of use. If the fraction is lyophilized, at time of use, it is preferred that the fraction be reconstituted by addition of distilled water.

The thrombin blood fraction can be in virtually any form, for example, a solution, suspension, emulsion or solid, with a solution being preferred. Thus, for example, such fraction can be a liquid, gel, paste or salve. Also, of course, the fraction can be in the form of a granule.

If the thrombin blood fraction is in a solid form, then the concentration of the thrombin blood fraction can be determined by dissolving it in a solution and then measuring the thrombin concentration. If the resulting thrombin concentration is from about 1 NIH unit/ml to about 2,000 NIH units/ml, then the thrombin blood fraction is within the scope of the subject invention.

4.1. Method for Preparation of the Thrombin Blood Fraction

The thrombin blood fraction of the subject invention can be prepared by any method known or to be developed. Also, the thrombin blood fraction can be prepared in a device as described in the patent application U.S. Pat. No. 5,480,378, the disclosure of which is incorporated herein by reference.

4.1.1. Method for Preparation of the Thrombin Blood Fraction by Formation of the Euglobulin Fraction from Plasma Whole blood can be withdrawn from an individual animal, e.g., a human, and preferably in the presence of an anticoagulant. Any anticoagulant can be utilized so long as it does not act by directly inactivating thrombin. Suitable anticoagulants are heparin, EDTA, citrate or any other agent that can, directly or indirectly, prevent the formation of thrombin, with citrate being preferred.

The plasma, which contains the prothrombin, is then separated from the whole blood. Any separation technique can be utilized, for example, sedimentation, centrifugation or filtration. Centrifugation can be carried out at about 1,500 to about 3,000 g. for about 10 minutes. The supernatant, which contains the plasma, can be removed by standard techniques. If it is desired to obtain a thrombin blood fraction that contains growth factors, then such centrifugation should be at about 125 g. for about 20 minutes or 1,000 g. for about 2 to 3 minutes. The thrombin blood fraction of the subject invention will then contain growth factors, which are released from the platelets during the conversion of prothrombin to thrombin.

The plasma in then treated, for example, by dilution with distilled water, followed by the addition of acid, e.g., citric acid, to lower the ionic strength to less than about 100 millimolar, preferably less than about 50 millimolar and most preferably from about 20 to about 40 millimolar and lower the pH to about 4.5 to about 6 and preferably to from about 5 to about 5.5. Lactic acid or acetic acid are also suitable acids. Generally, a weight ratio of the plasma:distilled water or acid of from about 1:5 to about 1:50, with 1:10 being preferred.

This treatment, i.e., the lowering of the ionic strength and pH of the plasma, results in the formation of a precipitate that is generally referred to as the "euglobulin fraction." The euglobulin fraction contains the prothrombin, fibrinogen and many other blood proteins, but is substantially free of antithrombin III.

Rather than diluting the plasma to lower the ionic strength, and before acidifying the plasma, the ionic strength can be lowered by dialyzing the plasma by placing the plasma in a dialysis bag, which is then placed in distilled water. The dialysis permits the ions to diffuse out of the plasma, thereby lowering the ionic strength. A suitable dialysis bag is composed of cellulose nitrate. Also, the ionic strength can be lowered by diafiltration or occlusion chromatography.

The euglobulin fraction can be prepared as described in A. Quick, Production of Thrombin From Precipitate Obtained by Acidification of Diluted Plasma, Am. J. Physiol., 183:114-118 (1955) and R. Biggs and R. G. Macfarlane, Human Blood Coagulation, pages 375-376, Blackwells Scientific Publications, Oxford, 3rd Edition (1962), the disclosures of which are incorporated herein by reference.

The excess fluid can then be separated from the euglobulin fraction by, for example, centrifugation, filtration or sedimentation. Centrifugation can be carried at about 1,500 g. for about 2 to about 5 minutes.

The prothrombin of the euglobulin fraction is then redissolved and converted to thrombin, thereby forming a thrombin blood fraction of the subject invention. This can be carried out by solubilizing the euglobulin fraction in a physiologically acceptable solution, e.g., saline, in an amount equal to or preferably less than (about 10%) the original amount of plasma. An alkaline buffer can be added in an amount to raise the pH of the solution to about 6 to about 8 and preferably to about 6.5 to about 7.5. Nonlimiting examples of suitable alkaline buffers include sodium hydroxide, potassium hydroxide, calcium hydroxide, bicarbonate buffers such as sodium bicarbonate and potassium bicarbonate, salts of acetic acid and salts of sulfuric acid. Preferred alkaline buffers include: Sodium carbonate/bicarbonate pH 7.0, Sodium bicarbonate/NaOH pH 7.0, 1.5M Glycine/NaOH pH 6.5-7.5. Bis hydroxyethylaminoethane sulphonic acid (BES) pH 7.5, Hydroxyethylpiperazine propane sulphonic acid (EPPS) pH 7.5, Tricine pH 7.5, Morpholino propane sulphonic acid (MOPS) pH 7.0, Trishydroxymethyl aminoethane sulphonic acid (TES) pH 7.0 and Cyclohexylaminoethane sulphonic acid (CHES) pH 7.0; with Sodium carbonate/bicarbonate pH 6.5-7.5 Bis hydroxyethylaminoethane sulphonic acid (BES) pH 7.5, Hydroxyethylpiperazine propane sulphonic acid (EPPS) pH 7.5 and Trishydroxymethyl aminoethane sulphonic acid (TES) pH 7.5 being most preferred.

Calcium is added to the neutral solution in order to convert the prothrombin to thrombin. Of course, the calcium can be part of the alkaline buffer. Calcium can be added in the form of, for example, calcium chloride. The amount of calcium added should be sufficient to convert an amount of prothrombin to thrombin that is sufficient for the intended medical use. Furthermore, the reaction should be permitted to occur for a period of time sufficient to convert enough of the prothrombin to thrombin that is sufficient for the intended medical use. Generally, from about 5 millimolar to about 50 millimolar calcium chloride is sufficient.

Also, rather than adding a source of calcium ions, prothrombin activating enzymes from snake venoms can be utilized. For example, snake venom from Eccis carinatus or the Australian Tiger snake can be utilized.

As the thrombin forms, it converts the fibrinogen to fibrin, which forms a fibrin clot. It is preferred to remove the fibrin clot, which can be carried out by, for example, wrapping the fibrin clot around a stirring rod or collecting the fibrin onto glass beads.

4.1.2. Method for Preparation of Thrombin Blood Fraction by Diluting Whole Blood In a preferred embodiment, the thrombin blood fraction can be prepared by initially preparing a prothrombin blood fraction from whole blood comprising:

(a) diluting whole blood to an ionic strength of less than about 100 millimolar;

(b) separating plasma from said whole blood;

(c) lowering the pH of said plasma to precipitate a prothrombin blood fraction; and (d) separating said prothrombin blood fraction from said plasma.

The prothrombin blood fraction is then redissolved and converted to thrombin, i.e., the thrombin blood fraction of the subject invention is formed, which can then be utilized in a medical procedure in an animal, e.g., as a component of a fibrin sealant. This method provides a thrombin blood fraction of the subject invention, which can be prepared in only about 45 minutes!

Specifically, whole blood is drawn from an individual animal. The whole blood is then immediately (within about five minutes) diluted in order to lower the ionic strength to less than about 100 millimolar, preferably less than about 50 millimolar and preferably to from about 20 to about 40 millimolar. It should be noted that since the whole blood is diluted immediately, there is no need for the use of an anticoagulant. Any physiologically acceptable solution at physiological osmotic pressure can be utilized to lower the ionic strength, e.g., a glucose aqueous solution such as a 5.5% isotonic aqueous glucose solution.

The plasma is then separated from the whole blood. Any separation technique can be utilized, for example, sedimentation, centrifugation or filtration. Centrifugation can be carried out at about 1,500 to about 3,000 g. for about 5 to about 10 minutes. The supernatant, which contains the plasma, can be removed by standard techniques.

The plasma fraction is then acidified, thereby resulting in the formation of a prothrombin blood fraction, which is generally referred to as the euglobulin fraction, which is a precipitate. The plasma fraction can be acidified with, for example, citric acid, lactic acid or acetic acid. The pH should be lowered to from about 4.5 to about 6 and preferably to from about 5 to about 5.5.

The excess fluid can then be separated from the prothrombin blood fraction by, for example, centrifugation, filtration or sedimentation. Centrifugation can be carried out at about 1,500 g for about 2 to about 5 minutes. This prothrombin blood fraction contains prothrombin, fibrinogen and many other blood proteins, but does not contain antithrombin III. The prothrombin blood fraction is then redissolved and the prothrombin is converted to thrombin. Any physiologically acceptable solution, e.g., saline, can be utilized to redissolve the prothrombin fraction. Furthermore, only a small volume of solution is required to redissolve the prothrombin fraction. It is believed that only from about 0.4 ml to about 1 ml of solution is required if about 17 ml of whole blood was initially drawn. An alkaline buffer can be added in an amount to raise the pH of the solution to about 6 to about 8 and preferably to about 6.5 to about 7.5. Nonlimiting examples of suitable alkaline buffers include sodium hydroxide, potassium hydroxide, calcium hydroxide, bicarbonate buffers such as sodium bicarbonate and potassium bicarbonate, tri-metal salts of citric acid, salts of acetic acid and salts of sulfuric acid. Preferred alkaline buffers include: Sodium carbonate/bicarbonate pH 6–8, Sodium bicarbonate/NaOH pH 6–8, Glycine/NaOH pH 6–8, Bis hydroxyethylaminoethane sulphonic acid (BES) pH 6–8, Hydroxyethylpiperazine propane sulphonic acid (EPPS) pH 6–8, Tricine pH 6–8, Morpholino propane sulphonic acid (MOPS) pH 6–8, Trishydroxymethyl aminoethane sulphonic acid (TES) pH 6–8 and Cyclohexylaminoethane sulphonic acid (CHES) pH 6–8; with Sodium carbonate/bicarbonate pH 6–8 Bis hydroxethylaminoethane sulphonic acid (BES) pH 6–8, Hydroxyethylpiperazine propane sulphonic acid (EPPS) pH 6–8 and Trishydroxymethyl aminoethane sulphonic acid (TES) pH 6–8 being most preferred.

Calcium is added to the neutral solution in order to convert the prothrombin to thrombin. Of course the calcium can be part of the alkaline buffer. Calcium can be added in the form of form of, for example, calcium chloride. The amount of calcium added should be sufficient to convert an amount of prothrombin to thrombin that is sufficient for the intended medical use. Furthermore, the reaction should be permitted to occur for a period of time sufficient to convert enough of the prothrombin to thrombin that is sufficient for the intended medical use. Generally, from about 5 millimolar to about 50 millimolar calcium chloride is sufficient. It has been observed that at about 25 minutes of reaction sufficient amounts of thrombin are formed for most medical uses of the thrombin blood fraction of the subject invention.

Also, rather than adding a source of calcium ions, prothrombin activating enzymes from snake venoms can be utilized. For example, snake venom from Eccis carinatus or the Australian Tiger snake can be utilized.

As the thrombin forms, it converts the fibrinogen to fibrin, which forms a fibrin clot. It is preferred to remove the fibrin clot, which can be carried out by, for example, wrapping the fibrin clot around a stirring rod or collection of the fibrin onto glass beads.

4.1.3. Preparation of Thrombin Blood Fraction by Removing or Inactivating Antithrombin III from Plasma In an alternative method, the thrombin blood fraction of the subject invention can be prepared by withdrawing whole blood from an individual animal, e.g., a human, and preferably in the presence of an anticoagulant. Any anticoagulant can be utilized. Suitable anticoagulants are heparin, EDTA, citrate or any other agent that can, directly or indirectly, prevent the formation of thrombin, with citrate being preferred.

The plasma, which contains the prothrombin, is then separated from the whole blood. Any separation technique can be utilized, for example, sedimentation, centrifugation or filtration. Centrifugation can be carried out at about 3,000 g. for about 10 minutes. The supernatant, which contains the plasma, can be removed by standard techniques.

Antithrombin III is then removed from the plasma or is inactivated. For example, the pH of the plasma can be lowered to at least to about 5. Such lowering of pH inactivates antithrombin III; otherwise antithrombin III would prevent the conversion of prothrombin to thrombin. Antithrombin III can be inactivated by any technique. For example, by the addition of 0.05 ml of 5 mol./liter HCl per 1.0 ml plasma. After about 10 to about 20 minutes of incubation, the plasma can be neutralized with 0.05 ml of 5 mol./liter NaOH per ml of plasma.

Rather than inactivating the antithrombin III, the antithrombin III can be removed from the plasma by passing the plasma through a column that binds antithrombin III, e.g., a heparin column or a column with antibodies to antithrombin III.

The plasma fraction, which contains prothrombin, is then treated to convert prothrombin to thrombin. This can be carried out by, for example, the addition of a source of calcium ions, as described above, or by the addition of 0.1 ml $CaCl_2$ of 0.36 mol./liter per ml of plasma. Also, rather than adding a source of calcium ions, prothrombin activating enzymes from snake venoms can be utilized. For example, snake venom from Eccis carinatus or the Australian Tiger snake.

As the thrombin forms, it converts the fibrinogen to fibrin, which forms a fibrin clot. It is preferred to remove the fibrin clot, which can be carried out by, for example, wrapping the fibrin clot around a stirring rod or collection of the fibrin onto glass beads.

The resulting plasma is a thrombin blood fraction of the subject invention.

4.1.4. Method for the Preparation of a Thrombin Blood Fraction by Diluting with an Acid Solution Directly By the known process for preparing thrombin from plasma, plasma is diluted in the ratio 1:10 with water, whereafter a pH-reducing acid is added, such as acetic acid, with the result that the pH-value is about 5.0 to 5.3. The mixture is then centrifuged for 20 min. at 2,000 g. The resulting precipitate contains different coagulation factors, such as inter alia prothrombin and fibrinogen. When the excess fluid has been removed, the precipitate is dissolved in a physiological solution, preferably a 0.9% sodium chloride solution, whereafter a pH-value-increasing agent, such as sodium carbonate, is added until the pH-value is about 7.9. When the precipitate has been dissolved, calcium chloride is added and causes the conversion of the prothrombin into thrombin by a conventional, so-called coagulation cascade. The resulting thrombin causes a conversion of fibrinogen into fibrin, whereafter the thrombin is separated by centrifuging and then subjected to a succeeding purification (column purification).

Another aspect of the subject invention is that the diluting step is performed directly with a diluted acid solution, e.g., 0.4% acetic acid, by the centrifuging step being performed in a container with a relatively large flat precipitation surface, by the physiological solution, with, the agent for increasing pH, and the calcium chloride being added at the same time to the precipitate as a mixture, whereby said precipitate is dissolved and then coagulates while forming fibrin, and by the thrombin then being removed.

As a result, it is now possible to prepare thrombin from plasma of autologous blood in a relatively quick way, which is in particular due to the fact that the precipitation is performed in a container with a relatively large flat precipitation surface. A quick and complete dissolution is thereby ensured of the precipitate containing prothrombin and fibrinogen. The complete dissolution is important before the presence of calcium chloride causes the conversion of prothrombin to thrombin. A too early thrombin formation leads to fibrin formation and the fibrin will bind the added fluid, whereby the dissolution of the precipitate stops and cannot continue until said fluid has again been passed out of the fibrin. The relatively small amount of precipitate spread over a comparatively large surface area provides complete dissolving of said precipitate by addition of the combined mixture of physiological solution, with the agent for increasing pH, and calcium chloride before the thrombin has been formed through said coagulation cascade and starts the formation of fibrin.

Moreover according to the invention, the mixture may be admixed with a plasminogen catalyst, such as streptokinase, before being added to the precipitate with the effect that the following separation of thrombin from fibrin is promoted.

According to the invention, the mixture added to the precipitate can advantageously be set to increase the pH-value to 6.5, whereby the resulting active thrombin is found to obtain the best keeping qualities as the thrombin has a tendency to become inactive on standing, which is usually the case in connection with enzymes. In addition, the dissolved precipitate can be transferred to a flexible material before the coagulation starts, said flexible material presenting a relatively large surface upon which the fibrin resulting from the coagulation can be deposited, whereafter the thrombin may be pressed out of the fibrin by the flexible material being subjected to a compaction. Exactly the obtained complete dissolving of the precipitate prior to formation of fibrin turned out to allow a quick transfer of the solution to a flexible material prior to said formation of fibrin. The flexible material ensures that the fibrin is deposited across a particularly large surface, the compaction of which facilitates the separation of thrombin from fibrin.

It is particularly preferred when the flexible material is a sponge with open pores.

The flexible material can be placed in a syringe, into which the dissolved precipitate can be absorbed and from which the thrombin can be squeezed out by an activation of the piston of the syringe. In this manner, a particularly easy separation of the thrombin from the flexible material is ensured.

Moreover, the centrifuging may according to the invention suitably be performed at about 1,500 g for about 5 min, which also accelerates the preparing of thrombin.

Thus, the subject invention comprises a process for preparing thrombin from human blood plasma, whereby the blood plasma is diluted to about 10 to 17% with water or another ion-intensity-reducing fluid and an acid to reduce pH to about 5.0 to 5.3, whereafter the mixture is centrifuged, and whereby the precipitate resulting from the centrifuging is admixed a physiological solution and calcium chloride, said physiological solution increasing pH to about 6 to 8, characterized by the diluting step being performed directly with a diluted acid solution, by the centrifuging step being performed in a container with a relatively large plane precipitation surface, by the physiological solution, with the agent for increasing pH, and the calcium chloride being added at the same time to the precipitate as a mixture, whereby said precipitate is dissolved and then coagulates while forming fibrin, and by the thrombin then being removed from the fibrin.

4.2. Acceleration of Thrombin Formation by Contacting Blood or Plasma with a Surface that Activates Blood Coagulation Factors XI and XII Another aspect of the subject invention is the preparation of a thrombin blood fraction wherein whole blood or plasma is contacted with a surface that activates blood coagulation factors XI and XII. It is believed that a negatively charged surface such as glass or kaolin, with glass being preferred, can provide such activation. Nonlimiting examples of glass surfaces are glass beads, glass wool, glass filters and glass capillary tubes.

The whole blood or plasma should contact the surface for a period of time sufficient to activate such blood coagulation factors, e.g., for about 5 to about 10 minutes. If the whole blood or plasma has not been treated with an anticoagulant, then the whole blood or plasma should be in contact with such a surface for not more than about 60 seconds, preferably less than about 30 seconds and more preferably about 15 seconds. Without the anticoagulant, and if the contact of the whole blood or plasma with the surface is too long, then fibrin clots will form prematurely.

It is preferred that plasma be exposed to a surface of about 4 $cm^2$ to about 60 $cm^2$, preferably from about 10 $cm^2$ to about 30 $cm^2$ and most preferably about 20 $cm^2$ of such surface for each milliliter of plasma. Also, it is preferred that whole blood be exposed to a surface of from about 2 $cm^2$ to about 30 $cm^2$, preferably from about 5 $cm^2$ to about 15 $cm^2$ and most preferably about 10 $cm^2$ of such surface for each milliliter of whole blood.

It is believed that the contacting of the plasma or whole blood with a surface that can activate factors XI and XII accelerates the conversion time of prothrombin to thrombin. Thus, a thrombin blood fraction can be prepared in an extremely short period of time.

This activation of factors XI and XII can be utilized to accelerate the preparation of any thrombin blood fraction, regardless of how the fraction is made and regardless of its purity and specific activity. However, it is essential that the thrombin blood fraction be substantially free of active antithrombin III. It is essential that the antithrombin III either be removed from or inactivated in the thrombin blood fraction prior to converting the prothrombin to thrombin. Otherwise, antithrombin III will prevent the conversion of the prothrombin to thrombin and/or inactivate the thrombin. It is also preferred that the thrombin blood fraction be substantially free of fibrinogen and fibrin. For example, with respect to the activation when the thrombin blood fraction is prepared by means of the euglobulin fraction as described in Section 4.1.1., the contacting of the plasma should be carried out immediately prior to the dilution of the plasma. When a thrombin blood fraction is prepared by diluting whole blood, as described in Section 4.1.2., the contacting of the whole blood should be carried out immediately prior to the dilution of the whole blood. For example, this contacting step can be carried out by withdrawing whole blood into a syringe that contains, for example, glass beads. After not more than about 60 seconds, the whole blood is discharged from the syringe and the thrombin blood fraction of the subject invention is then prepared, as described above.

4.3. The Uses of the Thrombin Blood Fraction of the Subject Invention

The thrombin blood fraction of the subject invention can be utilized in any medical procedure, known or to be developed, in an animal, including vetinary procedures. Any species of animal is suitable, but, of course, humans are preferred.

The thrombin blood fraction can be employed as a component of a fibrin sealant or can be employed alone just as conventional thrombin preparations have been employed. The thrombin blood fraction is utilized by contacting the desired site of the animal with the thrombin blood fraction. For the purpose of the subject invention, the "desired site" is that location in or on an animal where one desires to form a fibrin clot. What or where the desired site is depends on the use of the thrombin blood fraction of the subject invention.

The use of the thrombin blood fraction as a component of a fibrin sealant, can be utilized for connecting tissues or organs, stopping bleeding, healing wounds, sealing a surgical wound, use in vascular surgery include providing hemostasis for stitch hole bleeding of distal coronary artery anastomoses; left ventricular suture lines; aortotomy and cannulation sites; diffuse epimyocardial bleeding seen in reoperations; and oozing from venous bleeding sites, e.g. at atrial, caval, or right ventricular levels. The subject invention is also useful for sealing of dacron artery grafts prior to grafting, sealing tissues outside the body, producing fibrin rafts for cell growth, stopping bleeding from damaged spleens (thereby saving the organ), livers, and other parenchymatous organs; sealing tracheal and bronchial anastomoses and air leaks or lacerations of the lung, sealing bronchial stumps, bronchial fistulas and esophageal fistulas; for sutureless seamless healing ("Zipper" technique), and embolization in vascular radiology of intracerebral AVM's, liver AVM's, angiodysplasia of colon, esophageal varices, "pumping" GI bleeders secondary to peptic ulcers, etc. The subject invention is further useful for providing hemostasis in corneal transplants, nosebleeds, post tonsillectomies, teeth extractions and other applications. See G. F. Gestring and R. Lermer, Vascular Surgery, 294–304, September/October 1983.

The thrombin blood fraction of the subject invention can be employed alone to staunch oozing hemorrhages or hemorrhages in hollow organs. The thrombin blood fraction can also be utilized in the treatment of damaged live animal tissue by utilizing the fraction to activate the release of the materials, i.e., plated-derived factors, from platelets, wherein such materials can be utilized to heal damaged tissue. See U.S. Pat. No. 5,165,938, the disclosure of which is incorporated by reference. The thrombin blood fraction can also be utilized to assist in the cell culture growth of keratinocytes and to assist in the autologous transplantation of keratinocytes, or any other skin-derived cells, e.g., fibroblasts. See V. Ronfard et al., Burns 17:181–184 (1991); H. Broly, and J. Hunyadi et al., J. Dermatol. Surg. Oncol. 1:75–78 (1988) and U.S. Pat. No. 5,474,770, the disclosure of which is incorporated herein by reference. Also, the thrombin blood fraction can be placed on a solid support, e.g., bandage, suture, prosthesis, or dressing, that will be in contact with the desired site. Such support is then placed in contact with the desired site until, for example, the fibrin clot forms.

The dosage of the thrombin blood fraction depends on its particular use, but the dosage should be an effective amount for the composition to perform its intended use. Generally, it is believed that from about 0.5 ml to about 5 ml of the thrombin blood fraction is sufficient. However, depending on the use, the dosage can range from about 0.05 ml to about 40 ml.

If the thrombin blood fraction is utilized as a component of a fibrin sealant, then the fibrin sealant can be applied to the desired site with, for example, a double-barrelled syringe. The double-barrelled syringe can be Y-shaped, thereby permitting the mixing of fibrinogen and the thrombin blood fraction immediately prior to the contacting step. Also, rather than a Y-shaped double-barrelled syringe a double-barrelled syringe with two openings can be utilized. This permits the simultaneous contacting of the desired site. Also, the compositions of the double-barrelled syringe can be sprayed onto the desired site. See H. B. Kram et al., The American Surgeon, 57:381 (1991). Also, if the blood fraction is employed as a component of a fibrin sealant, then autologous fibrinogen can be utilized, thereby rendering the entire fibrin sealant autologous. Also, if the thrombin blood fraction is employed alone, then the fraction can be applied to the desired site with a single-barrelled syringe.

It should also be noted that the thrombin blood fraction of the subject invention can further comprise a source of calcium ions, e.g., calcium chloride. The source of calcium ions assists in the conversion of fibrinogen to the fibrin clot. The amount of calcium ions should be the same as that utilized in conventional fibrin sealants. However, since the thrombin blood fraction may contain a source of calcium ions already due to the conversion of prothrombin to thrombin, an additional source of calcium ions may not be required. But, if more calcium is needed to form the fibrin clot than to form thrombin, then, as an option, excess calcium from what is required to form thrombin can be utilized so that no additional calcium need be added when the thrombin blood fraction is utilized in the medical procedure, e.g., as a component of a fibrin sealant.

EXAMPLES

Example I

Preparation of a Composition Containing a Thrombin Blood Fraction Obtained From 17 ml of Fresh Blood From a Human Adult Donor A puncture of the vein of a human was performed by a needle and 17 ml of blood was drawn into an empty 30 ml syringe. Immediately after drawing the blood, it was transferred to a 50 ml test tube containing 34 ml of a solution containing 5.5% glucose. The 50 ml test tube was placed in a centrifuge and centrifuged for 5 minutes at 1,500×g at room temperature. After centrifugation, 40 ml of the supernatant plasma/glucose solution was removed by a syringe, and transferred to a new 50 ml test tube.

By means of 1.07 ml of a 2.8% citric acid solution, the pH in the plasma/glucose solution was lowered to 5.2 and after a period of 10 minutes at room temperature, the solution was centrifuged at 18° C. at 1,500×g for 5 minutes. After centrifugation, the supernatant was drained off and the precipitate was dissolved in 0.424 ml of a solution containing 14 mmole/L of NaHCO$_3$ and 8 gram/L of NaCl. This precipitate contains fibrinogen, prothrombin and other blood proteins, but is substantially free of antithrombin III. The pH of this dissolved prothrombin containing euglobulin solution was 7.35.

Activation of the prothrombin was performed by the addition of 0.027 ml of a solution containing CaCl$_2$, 0.5 mole/L. From 12 to 17 minutes after the addition of the CaCl$_2$, the fibrinogen in the solution started to coagulate, and the fibrin thus formed was removed by means of a polystyrene spatula. Small samples were removed at different intervals and the thrombin concentration was measured. The results from the example are shown in Table I.

TABLE I

| time after Ca-addition | 10 min | 20 min | 30 min | 60 min | 120 min | 27 hour |
|---|---|---|---|---|---|---|
| NIH u/ml | 0 | 180 | 368 | 540 | 600 | 737 |

Example II

Preparation of a Composition Containing a Thrombin Blood Fraction Obtained From 17 ml of Fresh Glass Activated Blood From a Human Adult Donor In this experiment, the donor and the day for the performance was the same as used in Example I. A puncture of the vein of a human was performed by a needle and 20 ml of blood was drawn into a 30 ml syringe containing 20 grams of glass beads with a diameter of approximately 2 mm. The total surface area of the beads was approximately 230 cm$^2$ and, therefore, the surface area was about 11.5 cm$^2$ per ml of whole blood.

Immediately after drawing the blood, the syringe was turned gently for 10 to 15 seconds before 17 ml of the blood was transferred to a 50 ml test tube containing 34 ml of a solution containing 5.5% glucose. The 50 ml test tube was placed in a centrifuge and centrifuged for 5 minutes at 1,500×g at room temperature. After centrifugation, 40 ml of the supernatant plasma/glucose solution was removed by a syringe, and transferred to another 50 ml test tube. By means of 1.07 ml of a 2.8% citric acid solution, the pH was lowered to 5.2 and after a period of 10 minutes at room temperature, the solution was centrifuged at 18° C. at 1,500×g for 5 minutes.

After centrifugation the supernatant was drained off and the precipitate was dissolved in 0.424 ml of a solution containing 14 mmole/L of NaHCO$_3$ and 8 gram/L of NaCl. This precipitate contains prothrombin, fibrinogen and other blood proteins, but is substantially free of antithrombin III. The pH of this dissolved prothrombin containing euglobulin solution was 7.35.

Activation of the prothrombin was performed by the addition of a 0.027 ml of a solution containing CaCl$_2$, 0.5 mole/L. From 4 to 9 minutes after the addition of the CaCl$_2$, the fibrinogen in the solution started to coagulate, and the fibrin thus formed was removed by means of a polystyrene spatula. Small samples were removed at different intervals and the thrombin concentration was measured. The results are shown in Table II.

TABLE II

| time after Ca-addition | 10 min | 20 min | 30 min | 60 min | 120 min | 27 hour |
|---|---|---|---|---|---|---|
| NIH u/ml | 130 | 444 | 560 | 720 | 695 | 880 |

Thus, from Table II it is readily apparent that the glass activation accelerates the time required for the conversion of the prothrombin to thrombin. For example, at only 10 minutes after the addition of a source of calcium ions, 130 NIH units/ml of thrombin activity was measured. In contrast, without glass activation, as in Example I, at 10 minutes after the addition of a source of calcium ions, there was no detectable thrombin activity.

Example III

Preparation of a Composition Containing a Thrombin Fraction Obtained From 17 ml of Fresh Blood From Human Adult Donors, Characterized by Low Specific Thrombin Activity In four experiments, performed as described in Example I, the thrombin concentration and the specific activity of thrombin were measured. The results are given in Tables III and IV where the pH value is the pH in the dissolved euglobulin fractions.

TABLE III

| A | | | thrombin measured from 15 min to 2 hours after dissolution of the euglobulin fraction. NIH u/ml | | | |
|---|---|---|---|---|---|---|
| donor | pH | E-280 | 15 min | 30 min | 60 min | 2 hr |
| JH | 6.96 | 25.8 | 142 | 483 | 661 | 779 |
| HJS | 6.35 | 26.7 | 0 | 56 | 942 | 1,238 |
| LK | 6.98 | 19.5 | 30 | 249 | 430 | 562 |
| KN | 6.21 | 31.5 | 0 | 142 | 616 | 725 |

(E-280 is a measurement of the total protein concentration in mg/ml).

TABLE IV

| B | Specific activity of thrombin measured from 15 min to 2 hours after dissolution of the euglobulin fraction. NIH u/mg protein | | | |
|---|---|---|---|---|
| donor | 15 min | 30 min | 60 min | 2 hr |
| JH | 5.5 | 19 | 26 | 30 |
| HJS | 0 | 2.1 | 35 | 46 |
| LK | 1.5 | 13 | 22 | 29 |
| KN | 0 | 4.5 | 20 | 23 |

Thus, the preparation of a thrombin blood fraction as described in Example I results in a thrombin blood fraction of a concentration and specific activity of the subject invention.

Example IV

Preparation of Thrombin from Whole Blood Using the Device of U.S. Pat. No. 5,480,378

Although any appropriate device can be employed, the device described in U.S. Pat. No. 5,480,378 was used for the preparation of thrombin in this Example. Before the blood was introduced into the device, 40 ml of a 5.5% glucose solution was introduced into the first chamber of the device through the filter mounted on the tubing.

Blood, 10 ml, was collected from human donors into a syringe and immediately thereafter transferred through the tubing into the glucose solution. The device was placed in a centrifuge and centrifuged for 5 min at 1,500×g. After centrifugation, the plasma/glucose solution was transferred into the second chamber with the red cells remaining in the first chamber. Through a sterile filter in tube 0.6 ml of 2.8% citric acid solution was introduced into the plasma/glucose solution. After 5 to 10 min, the device was placed in a centrifuge and centrifuged for 5 min at 1,500×g. After centrifugation the supernatant was transferred to the first chamber and the precipitate, the euglobulin fraction, remained in the second chamber. Through the sterile filter in tube 0.85 ml of a solution Contained 7.5 mM $NaHCO_3$, 52 mM NaCl and 30 mM $CaCl_2$ was introduced into the second chamber. The euglobulin precipitate was dissolved within 1–2 minutes, and transferred to a syringe connected to the second chamber. The syringe contained a polyurethane sponge facilitating the removal of the formed fibrin. Thrombin concentrations were measured after 30 min to 22 hours. The results are recited in Table V.

TABLE V

| Donor | plasma dilution | thrombin concentration NIH u/ml | | | |
|---|---|---|---|---|---|
| | | 30 min | 1 hour | 2 hour | 22 hour |
| RH-A | 11.9% | 186 | 240 | 231 | 279 |
| RH-B | 12.3% | 54 | 130 | 130 | 132 |
| RH-C | 11.7% | 178 | 186 | 180 | 192 |
| RH-D | 12.5% | 104 | 120 | 92 | 123 |

Example V

Preparation of Thrombin and Fibrinogen from Whole Blood Using a Device System Made from Two Inter-Connected Devices of U.S. Pat. No. 5,480,378, and the Use of Thrombin and Fibrinogen in a Fibrin Glue The device system consists of two devices as described in U.S. Pat. No. 5,480,378. The two tubings from the two devices were connected to the same cannula by means of a three-way connector. In the device used for the thrombin precipitation 5 glass beads, 3 mm in diameter, were placed in the second chamber. The syringe in the thrombin device was changed from being a 3 ml syringe in the fibrinogen device to a 1 ml syringe.

Before the blood was collected from the donor, citrate and glucose solutions were filled into first chambers of the two devices. Citrate, 5 ml of a 3.8% solution, was introduced into the first chamber of the fibrinogen device (hereafter named Device-F) through the filter mounted on the tubing. Glucose, 34 ml of a 5.5% solution was introduced into the first chamber of the thrombin device (hereafter named Device-T)) through the filter mounted on the tubing.

Blood, 45 ml was collected through the cannula into the first chamber in Device-F containing the citrate solution, and 17 ml was collected into the first chamber in Device-T containing the glucose solution. After collection of the blood, the separator-system was disconnected from the donor, and the tubing was sealed close to inlet. Both devices were placed in a centrifuge and centrifuged for 10 min at 1,500×g.

The separated plasma in Device-F was transferred to the second chamber And 2.5 ml of a 96% ethanol solution was introduced into the second chamber through the sterile filter in tube. The device was now placed into a ice-water bath for 20 minutes to reduced the temperature in the plasma/ethanol solution to approximately 0° to 4° C. At this temperature, 85% of the fibrinogen in plasma was precipitated. The device was now placed in a centrifuge and centrifuged for 5 min at 1,500×g.

The supernatant serum was transferred to the first chamber, and the solid fibrinogen was dissolved by incubation for 5 minutes at 37° C. The dissolved solution was transferred to the sterile syringe The concentration of fibrinogen was measured to be 31 mg/ml.

The separated plasma/glucose in Device-T was transferred into the second chamber with the red cells remaining in the first chamber. Through the sterile filter in tube 1.2 ml of a 2.8% citric acid solution was introduced into the plasma/glucose solution. After 5 to 10 min the device was placed in a centrifuge and centrifuged for 5 min at 1,500×g. After centrifugation, the supernatant was transferred to the first chamber and the precipitate, the euglobulin fraction, remained in the second chamber. Through the sterile filter in tube, 0.85 ml of a solution containing 7.5 mM $NaHCO_3$, 52 mM NaCl and 30 mM $CaCl_2$ was introduced into the second chamber. The euglobulin precipitate was dissolved within 1–2 minutes, and the fibrin formed during the activation of prothrombin to thrombin was collected onto 5 glass beads placed in the second chamber. After 15 minutes the thrombin solution was transferred to the syringe connected to the second chamber. Thrombin concentration was measured to be 248–340–372 NIR u/ml after 15–30–60 minutes, respectively.

The two syringes containing the fibrinogen and the thrombin were used as a double barreled syringe. The two solutions were expelled from the syringes and formed immediately a firm fibrin clot.

Example VI 54 ml of 0.04% HAc were added to 6 ml of plasma. This mixture was placed in a flat-bottomed container of the type known from the above PCT/DK91/00131. The container is of a circular cross section with an inner diameter of 4.5 cm. The pH-value was 5.3. The pH-value and the relatively low concentration of ions in the provided mixture ensure the following precipitation of the coagulation factors, inter alia prothrombin, as a precipitate by a centrifuging. The centrifuging was performed at 1,500 g for 5 min. Thus the centrifuging was relatively quickly terminated, which is due to the relatively short falling height and large precipitation surface. After removal of excess fluid, an 0.75 ml aqueous solution of 0.9% NaCl, 0.03% $Na_2CO_3$ and 25 mM $CaCl_2$ was added to the precipitate. After dissolving of the precipitate, the solution was sucked into a 2.5 ml syringe containing a polyurethane sponge. The formation of fibrin did not start until about 1 to 2 min. after the precipitate had become completely dissolved, and accordingly more than enough time for the sucking procedure. After termination of the formation of fibrin in the syringe, the thrombin solution could be expelled by squeezing the sponge by means of the piston of the syringe, the fibrin remaining depositing on the large surface of the sponge.

The dissolved precipitate had a pH-value of 6.5. Other amounts of $Na_2CO_3$ or another base or a buffer system can be used provided the pH-value is between 6.0 and 7.5, but an optimum balance between the keeping qualities of the thrombin and the capacity of the thrombin to accelerate the coagulation process is found at 6.5.

The thrombin was expelled from the syringe after 30 min, and a concentration of 256 NIH units per ml was obtained.

The thrombin concentration increased by time, but after 30 to 60 min a sufficient amount of thrombin was obtained for a conventional use in a fibrin sealant.

The preparation of thrombin was in the present Example produced from 12 ml of autologous blood and was terminated over a period of 45 to 60 min, i.e., almost simultaneously with the termination of the preparation of fibrinogen. The produced amount of thrombin was sufficient for being used in combination with fibrinogen produced from 45 ml of autologous blood in the manner described in PCT/DK91/00131.

The fibrin formed during the thrombin preparation has always a tendency to bind the thrombin. The release of this thrombin can, however, be promoted by the addition of a plasminogen catalyst, such as streptokinase, urokinase or t-PA (tissue plasminogen catalyst) optionally admixed with a physiological solution.

What is claimed:

1. In a method for the cell culture growth of keratinocytes from skin that utilizes thrombin, the improvement comprising thrombin that is derived from the same individual animal from which said skin is derived.

2. The method of claim 1 wherein said thrombin is a thrombin blood fraction comprising:

(a) a thrombin concentration of from about 1 NIH unit/ml to about 2,000 NIH units/ml, and (b) a specific activity of thrombin of from about 1 NIH unit/mg of blood protein to about 200 NIH units/mg of blood protein, wherein said thrombin blood fraction is substantially free of active antithrombin III.

* * * * *